US010835286B2

(12) United States Patent
Joie et al.

(10) Patent No.: US 10,835,286 B2
(45) Date of Patent: Nov. 17, 2020

(54) RECOVERABLE INTRA-UTERINE DEVICE

(71) Applicant: ANECOVA S.A., Lausanne (CH)

(72) Inventors: Michel Joie, Ernage (BE); Stéphane Riviere, Segny (FR); Julien Grogg, Villeneuve (CH)

(73) Assignee: ANECOVA S.A., Lausanne (CH)

( * ) Notice: Subject to any disclaimer, the term of this patent is extended or adjusted under 35 U.S.C. 154(b) by 227 days.

(21) Appl. No.: 15/769,305

(22) PCT Filed: Oct. 27, 2016

(86) PCT No.: PCT/EP2016/075877
§ 371 (c)(1),
(2) Date: Apr. 18, 2018

(87) PCT Pub. No.: WO2017/072204
PCT Pub. Date: May 4, 2017

(65) Prior Publication Data
US 2018/0310961 A1    Nov. 1, 2018

(30) Foreign Application Priority Data
Oct. 30, 2015  (FR) ..................................... 15 60439

(51) Int. Cl.
*A61B 17/46* (2006.01)
*A61B 17/435* (2006.01)
(Continued)

(52) U.S. Cl.
CPC ............ *A61B 17/43* (2013.01); *A61B 17/435* (2013.01); *A61B 2017/00862* (2013.01); *A61B 2017/00907* (2013.01); *A61B 2017/4216* (2013.01)

(58) Field of Classification Search
CPC .................. A61B 17/435; A61B 17/43; A61B 2017/4216; A61B 2017/00907; A61B 2017/00862
See application file for complete search history.

(56) References Cited

U.S. PATENT DOCUMENTS 3,797,492 A * 3/1974 Place ................... A61K 9/0004
604/890.1
5,135,865 A    8/1992 Ranoux
(Continued)

FOREIGN PATENT DOCUMENTS

EP    2 057 972    5/2009
WO    03/011200    2/2003

OTHER PUBLICATIONS

International Search Report issued in PCT/EP2016/075877 dated Nov. 28, 2016.
(Continued)

Primary Examiner — Christine H Matthews
Assistant Examiner — Joshua Daryl D Lannu
(74) Attorney, Agent, or Firm — Arent Fox LLP

(57) ABSTRACT

The disclosure relates to a retrievable intrauterine device which includes a recess suitable for containing one or more elements selected from the group that includes an embryo, male and/or female gametes, a fertilized oocyte, a non-fertilized ovule and a combination of the elements. The recess includes an inner wall made of a biocompatible polymer, the inner wall including at least one perforated portion having perforations with dimensions of between 1 pm and 10 pm, and an outer wall covering the inner wall, the outer wall being made of a biocompatible silicone elastomer and including at least one opening opposite said at least one
(Continued)

perforated portion of the inner wall. The use of the device relates to the preimplantation development of gametes and/or embryos.

23 Claims, 2 Drawing Sheets

(51) Int. Cl.
*A61B 17/43* (2006.01)
*A61B 17/00* (2006.01)
*A61B 17/42* (2006.01)

(56) References Cited

U.S. PATENT DOCUMENTS

| 5,505,716 | A | 4/1996 | Simmet |
| 2006/0228794 | A1 | 10/2006 | Ranoux et al. |
| 2009/0012352 | A1* | 1/2009 | Mock .................. A61B 17/435 600/34 |
| 2011/0060309 | A1* | 3/2011 | Lee ..................... A61K 9/0034 604/500 |

OTHER PUBLICATIONS

C. Blockeel et al: "An in vivo culture system for human embryos using an encapsulation technology: a pilot study", Human Reproduction, vol. 24, No. 4, Dec. 26, 2008 (Dec. 26, 2008). pp. 790-796.
R. Frydman et al: "INVO: a simple, Low cost effective assisted reproductive Technology", ESHRE MONOGRAPHS, vol. 2008, No. 1, Jul. 1, 2008 (Jul. 1, 2008), pp. 85-89.

* cited by examiner

RECOVERABLE INTRA-UTERINE DEVICE

CROSS-REFERENCE TO RELATED APPLICATIONS

This application is a national stage filing of International Patent Application PCT/EP2016/075877, filed Oct. 27, 2016, which claims priority France Patent Application 1560439, filed Oct. 30, 2015, the disclosure of each of which are hereby incorporated by reference.

The present invention concerns a recoverable intra-uterine device, used in particular for temporarily placing gametes and/or embryos in the uterus.

The present invention generally concerns the field of in-vivo and in-utero fecundation in assisted reproduction methods employing techniques of fertilization and/or pre-implantation development.

Intra-uterine systems that are implantable and recoverable through the body's passages have been known for several years Thus an intra-uterine device as described in document WO 03/011200 used in the in-vivo assistance in medically assisted reproduction processes is known.

Such a device is adapted to be placed in the uterine cavity for a period comprised between a few hours and a few days and enables the preimplantation development of an embryo.

The intra-uterine device comprises a housing adapted to contain the items to be encapsulated in the device, for example an embryo, male and/or female gametes, a fertilized oocyte, a non-fertilized ovum or for instance a combination of these items.

This encapsulation technique makes it possible to perform the fertilization and the development of an embryo inside a capsule placed in the uterus.

The Applicant has found that by transiently placing the capsule with an embryo in course of development in the uterus, the embryos so obtained were of better quality not only with regard to morphology but also with regard to their capacity to develop and to be re-implanted in the uterus later.

Thus, by obtaining embryos of better quality, it is possible to reduce the occurrences of multiple pregnancies by enabling the reimplantation of a single embryo with a greater chance of success than is obtained in the conventional methods of in-vitro assisted reproduction.

Furthermore, as the fertilization and preimplantation development take place directly in the uterus, the psychological repercussions on the couple may be high since the assisted reproduction process is closer to natural conception and requires higher implication by the couple.

The intra-uterine device makes it possible to place embryos in a natural environment during the preimplantation development phase, and thereby enables complex interactions between the endometrium of the uterus and the gametes and/or the embryos.

By minimizing the impact of the conditions of artificial culture (for example synthetic culture media) on the development of the embryo, the risk of alteration of the embryo by outside factors or by the lack of important substances for regulation and development is reduced.

In document WO 03/011200, the recoverable intra-uterine device comprises a housing of which the wall is formed from a porous permeable membrane, for example of polyether sulfone (PES).

The choice of such a porous membrane was initially guided to enable the protection of the gametes and/or embryos placed in the device while enabling the passage of nutrients, present in the uterine environment, into the housing of the device.

However, a porous permeable membrane is fragile and difficult to manipulate, in particular when loading and unloading the encapsulated items, or for instance when implanting and recovering the capsule inside the uterus.

It is indeed of the utmost importance not to deteriorate the capsule wall, which would induce the loss of the encapsulated items.

A recoverable intra-uterine device is also known from document FR 2 895 229 comprising a housing having a wall in which are formed perforations of which the dimensions are comprised between 10 µm and 150 µm.

However, the large size of these perforations can sometimes be of a detrimental character by enabling the passage of cells that are harmful to the development of the embryo.

The present invention is directed to solving at least some of the aforementioned drawbacks and to provide a recoverable intra-uterine device promoting exchanges with the uterus, reliably and reproducibly, and with easy manipulation, without risk of altering the housing wall.

To that end, the recoverable intra-uterine device according to the invention comprises a housing, said housing comprising an inside wall formed from a biocompatible polymer, said inside wall comprising at least one perforated part having perforations of dimensions comprised between 1 µm and 10 µm, and an outside wall covering said inside wall, the outside wall being formed from a biocompatible silicone elastomer and comprising at least one opening facing said at least one perforated part of the inside wall.

Thus, the housing comprises a double wall. The perforated part of the inside wall forms a barrier between the inside of the housing, which is for containing gametes or an embryo, and the uterus in which the intra-uterine device is placed. The inside wall thus enables intra-uterine exchanges thanks to the perforations.

Furthermore, the outside wall of the housing facilitates the manipulation of the housing by the biologist and/or the physician, by forming a protection made of a silicone elastomer.

The outside wall thus makes it possible to manipulate the housing without risk of deterioration or rupture of the inside wall, which is more fragile, comprising the perforated part to promote the exchanges with the uterus.

The inside wall of the recoverable intra-uterine device has the following features, alone or in combination with each other:
- the perforations have sizes comprised between 1 µm and 10 µm, and preferably between 2 µm and 8 µm;
- the inside wall is formed from polycarbonate;
- the inside wall has at least one perforated part comprising from 1 million to 5 million perforations per $cm^2$;
- the perforations are of substantially circular shape of diameter comprised between 1 µm and 10 µm, and preferably between 2 µm and 8 µm.

In an embodiment, the housing has a shape which is elongate in a longitudinal direction, the outside wall extending beyond the ends of the inside wall in the longitudinal direction.

The protection formed by the outside wall thus extends over the entire length of the housing, and beyond the inside wall.

Advantageously, the device comprises at least one plug mounted at an end of the housing in order to plug this during its use.

In an embodiment, the plug is mounted by friction at one of the ends of the inside wall of the housing and is partially covered by an end of the outside wall.

Such mounting ensures proper fluid-tightness of the plug closure system.

According to an example embodiment, the housing is of elongate cylindrical shape.

The outside wall comprises at least one opening extending in the longitudinal direction of the housing and over an angular sector of the housing comprised between 80° and 120°.

In practice, the inside wall comprises two perforated parts, which are diametrically opposite in the elongate cylindrical shape of the housing, and the outside wall comprises two openings respectively facing the two perforated parts of the inside wall.

The configuration of the housing results from a compromise between a high surface area for exchange with the uterus, at the location of the perforated parts of the inside wall, which are placed facing the openings of the outside wall, and good strength properties and manipulation of the intra-uterine device, thanks to the portions of outside wall.

Preferably, the inside wall and the outside wall are formed from transparent material.

The use of a transparent material makes it possible to facilitate the manipulation of the device, in particular when loading and unloading the device, thanks to viewing the gametes or embryos in the housing.

It is furthermore possible to observe from the outside of the device the development of the oocytes and/or embryos encapsulated inside the device.

In an application, the device contains at least one item chosen from the group comprising male and/or female gametes, a fertilized oocyte, a non-fertilized ovum or a combination of these items.

In another application, the device contains one or more embryos.

According to another aspect, the invention also concerns the use of the intra-uterine device for loading and/or unloading items chosen from the group comprising an embryo, male and/or female gametes, a fertilized oocyte, an unfertilized ovum and a combination of these items.

Still other particularities and advantages of the invention will appear in the following description.

In the accompanying drawings, given by way of non-limiting example:

Figure 1:
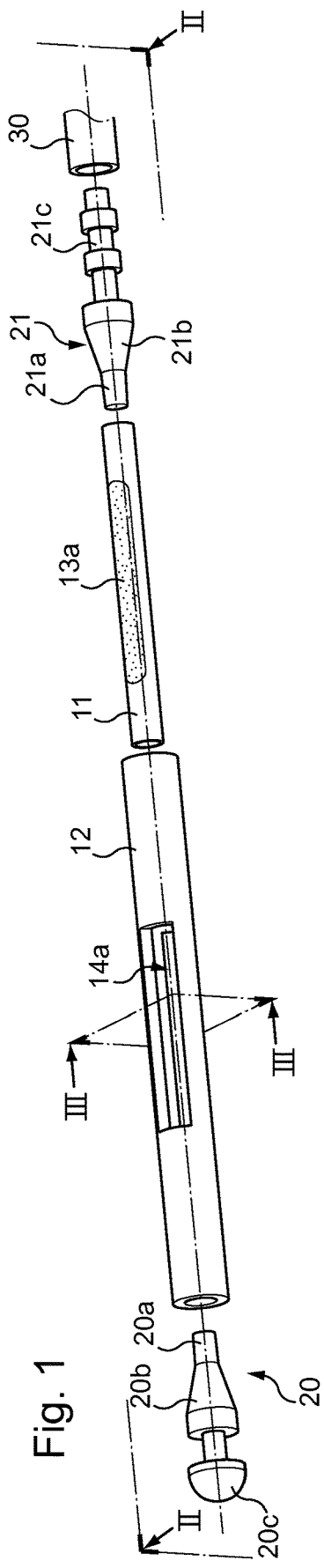
FIG. 1 is a partial exploded perspective view of a recoverable intra-uterine device according to an embodiment of the invention.
Figure 2:
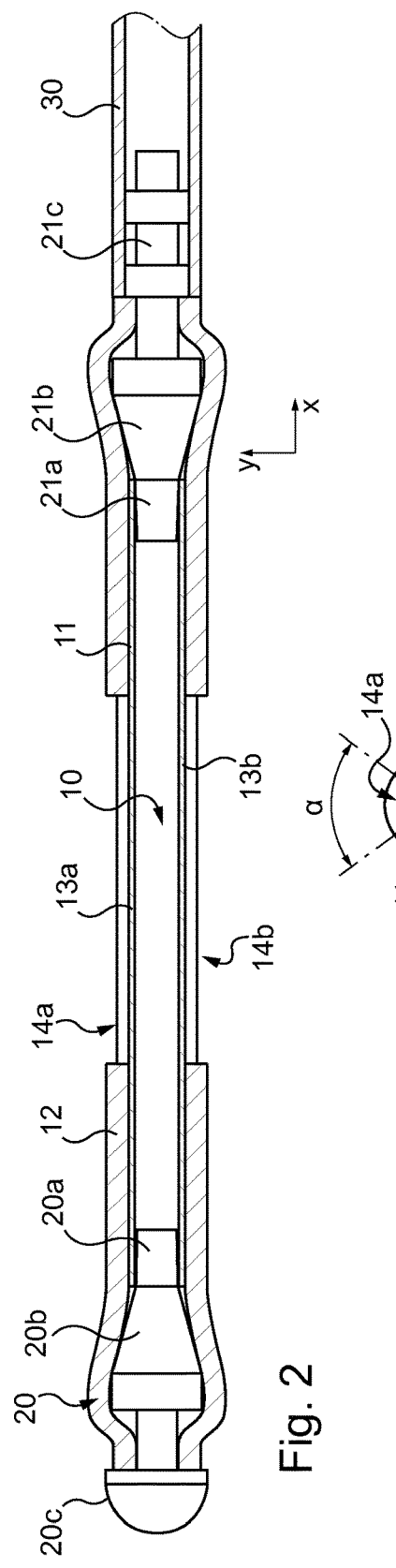
FIG. 2 is a view in longitudinal section on line II-II of the recoverable intra-uterine device of FIG. 1.
Figure 3:
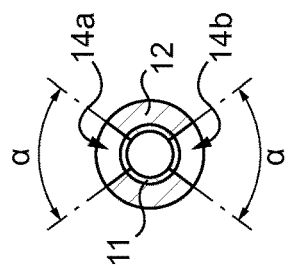
FIG. 3 is a cross-section view on line III-III of FIG. 1.

A description will first of all be made with reference to FIGS. 1 to 3 of an example embodiment of a recoverable intra-uterine device.

In general terms, the recoverable intra-uterine device comprises a housing 10 for containing various items employed in a process of medically assisted reproduction.

In particular, the housing 10 is configured to contain diverse items according to the state of progression of the fertilization process, for example male gametes and/or female gametes, an unfertilized ovum, or a fertilized oocyte, or one or more embryos.

It will be noted that the recoverable intra-uterine device is configured to contain one or other of these items according to the state of progression over time of the fertilization process.

The housing 10 is particular in that it comprises a double wall formed from an inside wall 11 and from an external wall 12.

The inside wall 11 is formed from a biocompatible polymer.

As the inside wall 11 is adapted to form the inside cavity of the housing 10, it is important for the material used to be of medical quality and not to create conditions that are detrimental to the development of embryos.

By way of example, the inside wall 11 may be formed of polycarbonate.

Of course, other types of biocompatible polymer could be used, for example a polyimide.

In order to allow exchanges with the intra-uterine environment, the inside wall 11 comprises at least one perforated part 13a, 13b.

In this embodiment, and on a non-limiting basis, the housing is of cylindrical shape which is elongate in a longitudinal direction X.

Thus, the inside wall 11 of the housing 10 also has an elongate cylindrical shape.

In this embodiment, as clearly illustrated in FIG. 2, the inside wall 11 comprises two perforated parts 13a, 13b which are diametrically opposite in the elongate cylindrical shape of the inside wall 11.

Of course, this embodiment is in no way limiting, and the inside wall could comprise a single perforated part or on the contrary, more than two perforated parts.

The Applicant has found that the perforations should have sufficient dimensions to promote exchanges with the nutrients present in the uterine environment, but without attaining dimensions such that the items contained in the housing 10 can escape into the uterus uncontrollably or that detrimental cells can enter the housing 10.

To that end, the perforations have dimensions comprised between 1 µm and 10 µm.

The perforations may of course have various shapes.

Whatever its shape, such a perforation will have dimensions comprised between 1 µm and 10 µm provided that a circle circumscribing that perforation has a diameter comprised between 1 µm and 10 µm.

More particularly, perforations having dimensions comprised between 2 µm and 8 µm are preferred for the intended applications.

As will appear below in the description of an embodiment of such a housing, the perforations may have a substantially circular shape of diameter comprised between 1 µm and 10 µm, and preferably between 2 µm and 8 µm.

The perforations are preferably disposed randomly and evenly in the perforated part 13a, 13b.

The density of these perforations must be sufficient in the perforated part 13a, 13b to create an adequate surface area for exchange with the intra-uterine environment.

By way of example, the perforated part 13a, 13b comprises one million to five million perforations per $cm^2$.

The outside wall 12 is formed from a biocompatible silicone elastomer.

Any type of silicone (or polymerized siloxane) taking the form of an elastomer may be used.

Other types of biocompatible elastomer may be used, for example a polyurethane thermoplastic elastomer or an elastomer of HCE type obtained by a hot curing process (HCE: initialism of Heat Curable Elastomer).

The outside wall 12 comprises at least one opening 14a, 14b for being positioned facing a perforated part 13a, 13b of the inside wall 11 when the outside wall 12 covers the inside wall 11.

In this embodiment, as the housing 10 has an elongate cylindrical shape, the outside wall 12 also has the general shape of an elongate cylinder.

On a non-limiting basis, in this embodiment in which the inside wall comprises two perforated parts 13a, 13b, the outside wall 12 comprises two openings 14a, 14b respectively facing the two perforated parts 13a, 13b of the inside wall 11.

Of course, the number and disposition of the openings 14a, 14b in the outside wall 12 are inherently linked to the number and the disposition of the perforated parts 13a, 13b of the inside wall 11.

In the embodiment described with reference to FIGS. 1 to 3, the outside wall 12 comprises two openings 14a, 14b which each extend in the longitudinal direction X of the housing 10.

As clearly illustrated in FIG. 3, the two openings 14a, 14b are diametrically opposite in the elongate cylindrical shape of the outside wall 12.

Each opening 14a, 14b extends over an angular sector a of the housing 10 comprised between 80° and 120°.

Preferably, when the outside wall 12 comprises two openings 14a, 14b, the angular sector a of each of the openings is comprised between 80° and 90°.

In this embodiment, two openings 14a, 14b having an angular sector a of the same value have been illustrated by way of example.

Of course, the invention is not limited to this embodiment and the openings of the outside wall 12 can have angular sectors of different values.

In particular, an embodiment can be preferred in which the sum of the angular sectors a of the openings provided in the outside wall 12 remains less than 180° such that the outside wall 12 can maintain sufficient rigidity in the length of the housing 10, in particular to enable holding of the closure system.

Similarly, the length in the longitudinal direction X of each opening 14a, 14b is comprised between a quarter and half of the length of the outside wall 12 of the housing 10, and preferably substantially equal to one third of that length.

Preferably, the biocompatible polymer used to produce the inside wall 11 and the biocompatible silicone elastomer used to produce the outside wall 12 are transparent materials, enabling the biologist and/or the physician to observe the inside of the capsule when it is manipulated.

On a non-limiting basis, a dimensional example of a housing 10 of a recoverable intra-uterine device will be given.

The inside wall 11 may have an inside diameter of 350 μm and an outside diameter of 500 μm.

The thickness of the inside wall 11 is thus substantially equal to 100 μm.

The length in the longitudinal direction X of the inside wall 11 is comprised between 4 mm and 6 mm in length.

Correspondingly, the outside wall 12 has an inside diameter comprised between 300 μm and 500 μm and preferably equal to 430 μm.

The outside diameter of the outside wall 12 is comprised between 700 μm and 800 μm and is preferably equal to 800 μm.

The thickness of the outside wall 12 is thus comprised between 200 μm and 400 μm.

The length in the longitudinal direction X of the outside wall 12 is comprised between 7 mm and 8 mm.

The windows 14a, 14b thus extend in the longitudinal direction X over a length comprised between 2 mm and 3 mm, and preferably have a length equal to 2.8 mm.

The angular sector of each opening 14a, 14b is substantially equal to 80°.

Independently of the specific dimensions indicated above, the housing has an elongate form in the longitudinal direction X, the outside wall 12 extending beyond the ends of the inside wall 11 in the longitudinal direction X.

A housing 10 is thus obtained with an outside wall 12 forming a protective cage around the inside wall 11.

A description will now be given by way of non-limiting example of a method of producing such a double-walled housing 10.

A cylindrical tube of silicone elastomer is employed cut to length to form the outside wall 12.

The openings 14a, 14b may be produced for example by cutting with a laser or for instance by cutting with a water jet under pressure.

Perforations are made over a tubular portion of polymer, such as polycarbonate to constitute the inside wall 11.

The inside wall 11 is cut to length, then inserted into the outside wall 12.

The perforated parts of the inside wall 11 appear exposed through the openings 14a, 14b of the outside wall 12.

To that end, "track etching" technology may for example be employed which is known for the production of porous polymer membranes.

In its principle, this "track etching" technology consists in irradiating the surface of the polymer forming the inside wall 11 by high energy heavy ions.

The bombardment by high energy heavy ions induces the formation of tracks by locally degrading the surface of the polymer.

The tracks are then revealed in the form of perforations (or pores) by selective chemical attack.

It is by way of example possible to use a caustic soda based chemical bath to create the perforations within the thickness of the inside wall 11.

Perforations are thus obtained which are randomly and evenly distributed over the perforated part 13a, 13b of the inside wall 11.

By way of non-limiting example, it is possible to obtain perforations in an inside wall 11 of polycarbonate which have a size substantially equal to 3.2 μm.

A housing 10 is thus obtained formed from a double wall, taking the general shape of an elongate cylinder open at both its ends.

In order to obturate the housing, the intra-uterine device comprises at least one plug mounted at an end of the housing 10.

In this embodiment, the intra-uterine device comprises two plugs 20, 21 respectively mounted at the distal and proximal ends of the housing 10.

The plugs 20, 21 may for example be produced from titanium.

As clearly illustrated in FIG. 2, each plug 20, 21 is mounted by friction at an end of the inside wall 11.

For this purpose, each plug 20, 21 comprises a first frusto-conical part 20a, 21a of which the outside diameter is, at its small base, slightly less than the inside diameter of the inside wall 11. The first frusto-conical part 20a, 21a widens to attain, at its larger base, an outside diameter slightly greater than the inside diameter of the inside wall 11.

Each first frusto-conical portion 20a, 21a is extended by a second frusto-conical portion 20b, 21b widening from the first frusto-conical portion 20a, 21a.

The second frusto-conical portion 20b, 21b is configured to be covered by one end of the outside wall 12 which extends beyond the ends of the inside wall 11, to an extender of the plug 20c, 21c.

The wider diameter of each plug 20, 21, and here the wide base of the second frusto-conical part 20b, 21b, has a dimension slightly greater than the inside diameter of the outside wall 12 such that the mounting of the plug 20, 21 is achieved by slight deformation of the outside wall 12 of the housing, providing perfect sealing for the mounting of the plug.

The distal plug 20 further comprises a first extender 20c having for example the shape of a nail head, enabling the physician or biologist to manipulate the distal plug 20 to enable the closing or the opening of the housing 10.

The proximal plug 21 is extended by a second extender 21c, forming a fastening stem 21c configured to be inserted by force into a connector 30 (partially illustrated in FIGS. 1 and 2).

Such a connector is described in particular in document FR 2 903 879 A1 and does not need to be described here in detail.

Only the essential parts of this connector are reviewed below with reference to FIG. 4.

Such a connector is configured for mounting a stabilizing arm, useful for holding the intra-uterine device in position in the uterus, as well as for the mounting of a removal thread.

Figure 4:
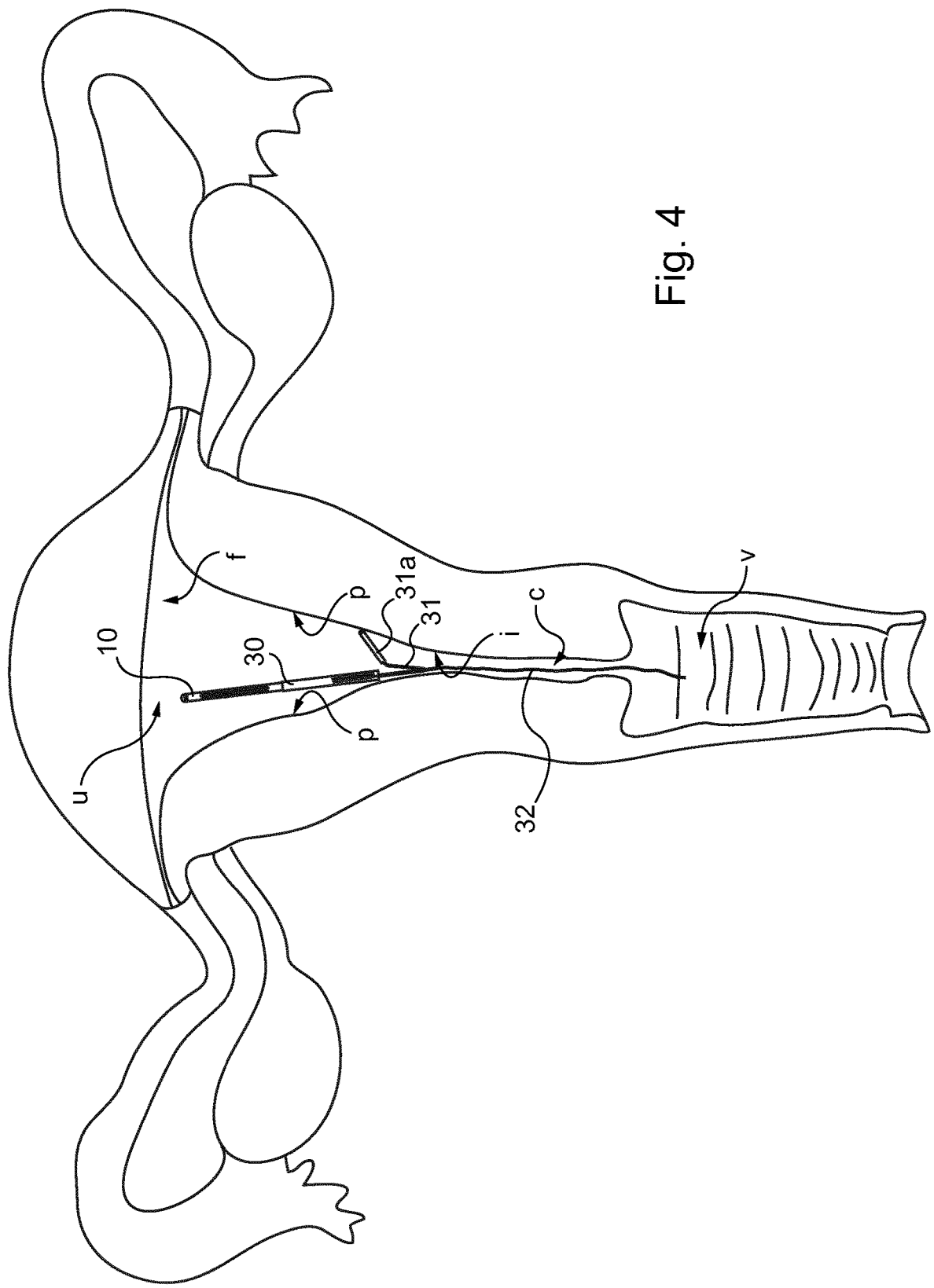
FIG. 4 is a cross-section view diagrammatically illustrating the recoverable intra-uterine device according to an embodiment placed in a uterine cavity.

As clearly illustrated in FIG. 4, the connector 30 comprises a cylindrical tube extending to the proximal end of the housing 10.

The cylindrical tube of the connector 30 is for example of silicone elastomer and is mounted by force at its distal end on the fastening stem 21c joined to the proximal plug 21.

A stabilizing arm 31 is fastened at the proximal end of the cylindrical tube of the connector 30.

In general terms, the stabilizing arm 31 can adopt a folded position, thus extending in the longitudinal direction X of the housing 10 and of the connector 30, and an extended position such as illustrated in FIG. 4 in which, by a spring effect, the stabilizing arm 31 unfolds, one end 31a of the arm coming locally into contact with the uterus u.

The stabilizing arm 31 can for example be formed of steel and may have at its end 31a a protective sleeve of silicone elastomer.

Furthermore, a removal thread 32 of nylon to enable the removal of the device from the uterus by pulling is fastened to the proximal end of the cylindrical tube of the connector 30.

The principle of use and of putting in place the intra-uterine device is similar to that described in document FR 2 903 879 A1

As clearly illustrated in FIG. 4, the intra-uterine device is inserted through the body's passages into the uterus by means of a transfer catheter (not shown).

The transfer catheter is next withdrawn enabling the stabilizing arm 31 to extend and hold the intra-uterine device in place for a few hours or a few days, enabling preimplantation development of the embryo in the intra-uterine environment.

Thanks to the porosity of the inside wall 11 of the housing 10, at the location of the perforated parts 13a, 13b, exchanges between the gametes and/or embryos contained in the intra-uterine device and the uterine fluids are promoted and enable optimal development of the embryo.

To that end, the intra-uterine device is placed in the uterus u near the fundus f and the end 31a of the stabilizing arm 31 comes into contact only with a very small portion of the endometrial wall at the location of the cervical canal i.

Thus, the endometrial layer that lines the uterine cavity at the fundus f, the corpus p and the cervical canal i have very little contact with the intra-uterine device, avoiding any deterioration of the endometrium which could be detrimental to the later reimplantation of the embryo.

Furthermore, the removal thread 32 extends through the cervix c to emerge in the vagina v and enable easy extraction of the device by the practitioner, simply by pulling.

Of course, the invention is not limited to the embodiments described above and numerous modifications may be made to those examples without departing from the scope of the invention.

The invention claimed is:

1. A recoverable intrauterine device comprising a housing adapted to comprise one or more of an embryo, male and/or female gametes, a fertilized oocyte, an unfertilized egg, or a combination thereof, wherein said housing comprises an inner wall made of a biocompatible polymer, said inner wall comprising at least one perforated portion having perforations of dimensions between 1 μm and 10 μm, and an outer wall covering said inner wall, the outer wall being made of a biocompatible silicone elastomer and comprising at least one opening facing said at least one perforated portion of said inner wall.

2. The recoverable intrauterine device of claim 1, wherein said perforations have dimensions between 2 μm and 8 μm.

3. The recoverable intrauterine device of claim 2, wherein the inner wall is made of polycarbonate.

4. The recoverable intrauterine device of claim 2, wherein said at least one perforated portion comprises from 1 million to 5 million perforations per $cm^2$.

5. The recoverable intrauterine device of claim 2, wherein the inside wall has ends in a longitudinal direction and the housing is of elongate shape in the longitudinal direction, said outer wall extending beyond the ends of said inner wall in the longitudinal direction.

6. The recoverable intrauterine device of claim 2, wherein the perforations have substantially a circular shape of diameter between 2 μm and 8 μm.

7. The recoverable intrauterine device of claim 1, wherein the inner wall is made of polycarbonate.

8. The recoverable intrauterine device of claim 7, wherein said at least one perforated portion comprises from 1 million to 5 million perforations per $cm^2$.

9. The recoverable intrauterine device of claim 7, wherein the perforations have substantially a circular shape of diameter between 1 μm and 10 μm.

10. The recoverable intrauterine device of claim 7, wherein the perforations have substantially a circular shape of diameter between 2 μm and 8 μm.

11. The recoverable intrauterine device of claim 1, wherein said inner wall comprising at least one perforated portion has 1 million to 5 million perforations per $cm^2$.

12. The recoverable intrauterine device of claim 1, wherein the perforations have substantially a circular shape of diameter between 1 μm and 10 μm.

13. The recoverable intrauterine device of claim 1, wherein the inside wall has ends in a longitudinal direction and the housing is of elongate shape in the longitudinal direction, said outer wall extending beyond the ends of said inner wall in the longitudinal direction.

14. The recoverable intrauterine device of claim 13, further comprising at least one cap mounted at one end of the housing, said at least one cap being frictionally mounted at one of said ends of the inner wall of said housing and being partially covered by one end of the outer wall.

15. The recoverable intrauterine device of claim 14, wherein said housing is of elongated cylindrical shape.

16. The recoverable intrauterine device of claim 1, wherein said housing is of elongated cylindrical shape.

17. The recoverable intrauterine device of claim 16, wherein the outer wall comprises at least one opening extending in a longitudinal direction of the housing and on an angular sector of the housing between 80° and 120°.

18. The recoverable intrauterine device of claim 17, wherein the inner wall comprises two perforated portions, diametrically opposed in said elongated cylindrical shape of the housing, and the outer wall comprises two openings respectively facing said two perforated portions of said inner wall.

19. The recoverable intrauterine device of claim 16, wherein the inner wall comprises two perforated portions, diametrically opposed in said elongated cylindrical shape of the housing, and the outer wall comprises two openings respectively facing said two perforated portions of said inner wall.

20. The recoverable intrauterine device of claim 1, wherein the inner wall and the outer wall are made of transparent material.

21. The recoverable intrauterine device of claim 1, wherein said device comprises at least one of male and/or female gametes, a fertilized oocyte, an unfertilized egg or a combination thereof.

22. The recoverable intrauterine device of claim 1, wherein said device contains one or more embryos.

23. The recoverable intrauterine device of claim 1, wherein the perforations have substantially a circular shape of diameter between 2 μm and 8 μm.

* * * * *